(12) United States Patent
Hooriani et al.

(10) Patent No.: US 11,311,188 B2
(45) Date of Patent: Apr. 26, 2022

(54) VISUAL AND MENTAL TESTING USING VIRTUAL REALITY HARDWARE

(71) Applicant: Micro Medical Devices, Inc., Calabasas, CA (US)

(72) Inventors: Ramin Hooriani, Calabasas, CA (US); Rafi Israel, Calabasas, CA (US)

(73) Assignee: Micro Medical Devices, Inc., Calabasas, CA (US)

( * ) Notice: Subject to any disclaimer, the term of this patent is extended or adjusted under 35 U.S.C. 154(b) by 341 days.

(21) Appl. No.: 16/024,509

(22) Filed: Jun. 29, 2018

(65) Prior Publication Data
US 2019/0014981 A1    Jan. 17, 2019

Related U.S. Application Data
(60) Provisional application No. 62/604,571, filed on Jul. 13, 2017.

(51) Int. Cl.
| | |
|---|---|
| *A61B 5/00* | (2006.01) |
| *A61B 3/00* | (2006.01) |
| *A61B 3/14* | (2006.01) |
| *A61B 3/032* | (2006.01) |
| *G16H 40/60* | (2018.01) |

(Continued)

(52) U.S. Cl.
CPC ............ *A61B 3/005* (2013.01); *A61B 3/0025* (2013.01); *A61B 3/0091* (2013.01); *A61B 3/032* (2013.01); *A61B 3/14* (2013.01); *G16H 40/60* (2018.01); *A61B 3/113* (2013.01); *A61B 5/0022* (2013.01); *A61B 5/16* (2013.01); *A61B 5/4064* (2013.01); *A61B 5/6898* (2013.01); *A61B 5/7445* (2013.01); *A61B 5/7455* (2013.01); *A61B 2090/502* (2016.02); *G16H 10/40* (2018.01); *G16H 50/20* (2018.01)

(58) Field of Classification Search
CPC .... H04N 13/111; H04N 7/181; H04N 13/344; G16H 30/40; G16H 40/20; G16H 40/40; G16H 50/20; G16H 40/60; G16H 10/40; A61B 1/00; A61B 2034/2065; A61B 2090/371; A61B 34/10; A61B 5/02438; A61B 5/165; A61B 3/00; A61B 3/005; A61B 3/0025; A61B 3/14; A61B 3/0091; A61B 3/032; A61B 3/113; A61B 5/16; A61B 5/6898; A61B 2090/502; A61B 5/0022; A61B 5/4064; A61B 5/7445; A61B 5/7455
USPC ................. 600/300, 558; 351/206, 208, 209
See application file for complete search history.

(56) References Cited

U.S. PATENT DOCUMENTS

| | | | |
|---|---|---|---|
| 5,880,812 A * | 3/1999 | Solomon ................ | A61B 3/024 351/209 |
| 6,120,461 A * | 9/2000 | Smyth .................... | A61B 3/113 600/558 |

(Continued)

*Primary Examiner* — May A Abouelela
(74) *Attorney, Agent, or Firm* — Smyrski Law Group, A P.C.

(57) ABSTRACT

An apparatus including a set of virtual reality goggles affixable to a patient is provided. The set of virtual reality goggles includes two central lenses employed to be positioned over the patient's eyes, securing means configured to secure a computing device to the set of virtual reality goggles, and means for determining a distance between the patient's eyes and the computing device. The set of virtual reality goggles is employable to test visual and/or mental attributes of the patient.

23 Claims, 7 Drawing Sheets

(51) Int. Cl.
  *G16H 10/40* (2018.01)
  *A61B 5/16* (2006.01)
  *A61B 90/50* (2016.01)
  *G16H 50/20* (2018.01)
  *A61B 3/113* (2006.01)

(56) References Cited

U.S. PATENT DOCUMENTS

| | | | | |
|---|---|---|---|---|
| 7,044,602 B2* | 5/2006 | Chernyak | A61B 3/1015 | 351/208 |
| 7,448,751 B2* | 11/2008 | Kiderman | A61B 3/113 | 351/205 |
| 7,465,050 B2* | 12/2008 | Migliaccio | A61B 3/113 | 351/209 |
| 7,486,988 B2* | 2/2009 | Goodall | A61B 5/04001 | 349/13 |
| 8,016,770 B2* | 9/2011 | Chiba | A61B 5/163 | 600/558 |
| 9,230,473 B2* | 1/2016 | Margolis | H04N 21/42202 | |
| 10,045,729 B2* | 8/2018 | Suarez | A61B 5/6814 | |
| 10,540,004 B2* | 1/2020 | Sanger | G06F 16/56 | |
| 2004/0070729 A1* | 4/2004 | Wiebe | A61B 5/6803 | 351/209 |
| 2005/0099601 A1* | 5/2005 | MacDougall | A61B 3/113 | 351/209 |
| 2005/0131663 A1* | 6/2005 | Bangs | G06F 19/00 | 703/11 |
| 2005/0216243 A1* | 9/2005 | Graham | G16H 50/50 | 703/11 |
| 2007/0038142 A1* | 2/2007 | Todd | G02B 27/0172 | 600/558 |
| 2007/0161875 A1* | 7/2007 | Epley | A61B 5/4023 | 600/301 |
| 2008/0058681 A1* | 3/2008 | Casali | A61B 5/4863 | 600/587 |
| 2008/0161673 A1* | 7/2008 | Goodall | A61B 5/04001 | 600/409 |
| 2010/0228144 A1* | 9/2010 | Labat | A61B 5/11 | 600/558 |
| 2011/0077548 A1* | 3/2011 | Torch | A61B 5/165 | 600/558 |
| 2011/0092805 A1* | 4/2011 | Estevez | A61B 5/055 | 600/419 |
| 2012/0035498 A1* | 2/2012 | Wilkins | A61B 5/1124 | 600/558 |
| 2012/0089049 A1* | 4/2012 | Suarez | A61B 5/7235 | 600/558 |
| 2012/0108909 A1* | 5/2012 | Slobounov | G16H 50/30 | 600/300 |
| 2012/0218285 A1* | 8/2012 | Crane | A61B 5/4023 | 345/589 |
| 2013/0222384 A1* | 8/2013 | Futterer | G02B 27/0103 | 345/426 |
| 2013/0308099 A1* | 11/2013 | Stack | A61B 5/163 | 351/209 |
| 2015/0042953 A1* | 2/2015 | Teller | H04H 60/46 | 351/209 |
| 2015/0382198 A1* | 12/2015 | Kashef | H04W 8/20 | 726/5 |
| 2016/0219078 A1* | 7/2016 | Porras | H04L 41/12 | |
| 2016/0234221 A1* | 8/2016 | Junuzovic | H04L 63/08 | |
| 2016/0259977 A1* | 9/2016 | Asbun | G16H 40/67 | |
| 2016/0320623 A1* | 11/2016 | Miyao | H04N 13/344 | |
| 2016/0324416 A1* | 11/2016 | Fateh | A61B 3/0033 | |
| 2016/0353094 A1* | 12/2016 | Rougeaux | G02B 27/0172 | |
| 2016/0366399 A1* | 12/2016 | Tempel | H04N 13/344 | |
| 2017/0010471 A1* | 1/2017 | Serrano Canovas | G02B 30/34 | |
| 2017/0053450 A1* | 2/2017 | Rodriguez | H04N 13/398 | |
| 2017/0064291 A1* | 3/2017 | Do | G09G 3/2003 | |
| 2017/0078645 A1* | 3/2017 | Aurigema | H04N 5/2256 | |
| 2017/0099478 A1* | 4/2017 | Cambridge | G06F 3/005 | |
| 2017/0102549 A1* | 4/2017 | Lee | G02B 27/0172 | |
| 2017/0102767 A1* | 4/2017 | Kim | G02B 27/017 | |
| 2017/0123234 A1* | 5/2017 | Sabovic | G02C 7/083 | |
| 2017/0154455 A1* | 6/2017 | Park | H04N 13/344 | |
| 2017/0252216 A1* | 9/2017 | Maeda | H04N 13/139 | |
| 2017/0281026 A1* | 10/2017 | Nick | A61B 5/7445 | |
| 2017/0296048 A1* | 10/2017 | Lahiri | A61B 5/0075 | |
| 2017/0296421 A1* | 10/2017 | Travers | A61H 5/00 | |
| 2018/0011333 A1* | 1/2018 | Ansay | G02B 30/37 | |
| 2018/0020910 A1* | 1/2018 | Maeda | A61B 3/005 | 351/223 |
| 2018/0075764 A1* | 3/2018 | Bachani | A61B 5/742 | |
| 2018/0088669 A1* | 3/2018 | Ramaprakash | A61B 5/6803 | |
| 2018/0103917 A1* | 4/2018 | Kim | A61B 5/24 | |
| 2018/0125352 A1* | 5/2018 | Schmid | A61B 3/0025 | |
| 2018/0165713 A1* | 6/2018 | O'Hanlon | G06Q 30/0276 | |
| 2018/0168444 A1* | 6/2018 | Foss | A61B 3/08 | |
| 2018/0256115 A1* | 9/2018 | Campbell | G16H 50/30 | |
| 2018/0332268 A1* | 11/2018 | Xiao | G02B 27/0172 | |
| 2018/0333092 A1* | 11/2018 | Roshan | A61B 5/18 | |
| 2019/0008441 A1* | 1/2019 | Guzik | A61B 5/486 | |
| 2019/0090775 A1* | 3/2019 | Quevedo | A61B 5/411 | |
| 2019/0142270 A1* | 5/2019 | Monhart | A61B 3/08 | 351/209 |

* cited by examiner

VISUAL AND MENTAL TESTING USING VIRTUAL REALITY HARDWARE

This application claims priority based on U.S. Provisional Patent Application Ser. No. 62/604,571, filed on Jul. 10, 2017, inventors Ramin Hooriani et al., the entirety of which is incorporated herein by reference.

BACKGROUND OF THE INVENTION

Field of the Invention

The present invention relates generally to testing the visual and mental health of patients, and more particularly to testing visual and mental health using virtual reality technology.

Description of the Related Art

Patients presenting in medical situations, such as testing of ocular health, are presented with devices dating back decades. Eye health is typically assessed using a device called a phoropter, where the patient sits in a chair, and an arrangement of lenses are swapped in and out in an effort to find the correct prescription for the patient, who is looking at an eye chart located several feet away.

The issue with such procedures is that the patient must travel to the office and the phoropter. Certain individuals cannot travel easily, while others are long distances from optometrists, and optometrists cannot efficiently and effectively transport such devices over long distances to patients. Further, phoropters tend to be limited in their abilities. Judging optical health frequently requires additional equipment to assess risks of glaucoma, etc.

Further, certain issues may arise that require a patient to view items and recount to physicians what they see. One example of this is head trauma or brain related issues, where a patient is asked to view items and state what he or she sees to a doctor. The doctor must control the items seen to some degree, and again, persons who cannot easily travel to a physician's office who has the necessary equipment are at a distinct disadvantage and in some cases may not be in a position to get the help they need.

More specifically, visual acuity tests are known and have been employed by physicians for decades. Drawbacks of existing visual testing devices include, for example, a setup such that 20 feet distance is maintained between patient and the visual acuity check screen. Conventional tests typically employ a Snellen chart, and the most popular types of Snellen charts cannot be used for children or persons lacking the ability to speak. Further, the health care professional must check on the patient as well as the Snellen chart to know if he/she is reading the chart correctly and to ensure the patient is covering one eye properly. Visual fields system and contrast sensitivity testing require large machines each requiring setup. Appropriate lighting conditions must be maintained in the patient testing room, and a conventional visual field test involves pressing a response button to confirm the visibility of light. Patients suffering from paralysis or muscular dystrophy or similar conditions are unable to perform this task.

Hence the drawbacks common to currently available visual acuity, visual fields, and contrast sensitivity tests include the fact that home-based reliable and calibrated tests that can be immediately shared with a doctor or health care entity are not available. Further, patients require an ophthalmologist/optometrist or other healthcare professional to be present, and the health care provider must train staff with detailed training programs to carry out these tests. Conventional testing practices cannot be administered to patients who cannot visit the hospital, such as patients in old age homes, disabled/wheelchair patients, patients belonging to under-developed countries.

Thus it would be beneficial to offer a solution for evaluating patient health in situations where the patient cannot get to heavy equipment needed, particularly in areas of optical and mental health. Such a solution would at least partially address issues with older methods of assessing patient health and diagnosing issues.

SUMMARY OF THE INVENTION

Thus according to one aspect of the present design, there is provided an apparatus comprising virtual reality goggles affixable to a patient, the virtual reality goggles comprising two central lenses employed to be positioned over the patient's eyes, securing means configured to secure a computing device to the set of virtual reality goggles, and means for determining a distance between the patient's eyes and the computing device. The set of virtual reality goggles is employable to test visual and/or mental attributes of the patient.

According to another aspect of the present design, there is provided an apparatus comprising virtual reality goggles affixable to a patient, the virtual reality goggles comprising two central lenses employed to be positioned over the patient's eyes, and means for determining distance between the patient's eyes and the two central lenses. The virtual reality goggles are employable to test visual and/or mental characteristics of the patient.

According to a further aspect of the present design, there is provided a system for testing ocular characteristics of a patient, comprising a controller configured to coordinate and perform visual testing, virtual reality goggles connectable to the controller and affixable to the patient, the virtual reality goggles comprising two central lenses employed to be positioned over the patient's eyes, and means for assessing position of the virtual reality goggles relative to the patient's eyes, including distance from the patient's eyes to a display element provided with the virtual reality goggles. The controller provides signals to and receives signals from the virtual reality goggles to test and assess visual and/or mental attributes of the patient.

These and other advantages of the present invention will become apparent to those skilled in the art from the following detailed description of the invention and the accompanying drawings.

BRIEF DESCRIPTION OF THE DRAWINGS

For a more complete understanding of the present disclosure, reference is now made to the following figures, wherein like reference numbers refer to similar items throughout the figures:

FIG. 4 shows one form of visual acuity test;

FIG. 5 is a line from a representative visual acuity test;

Figure 1:
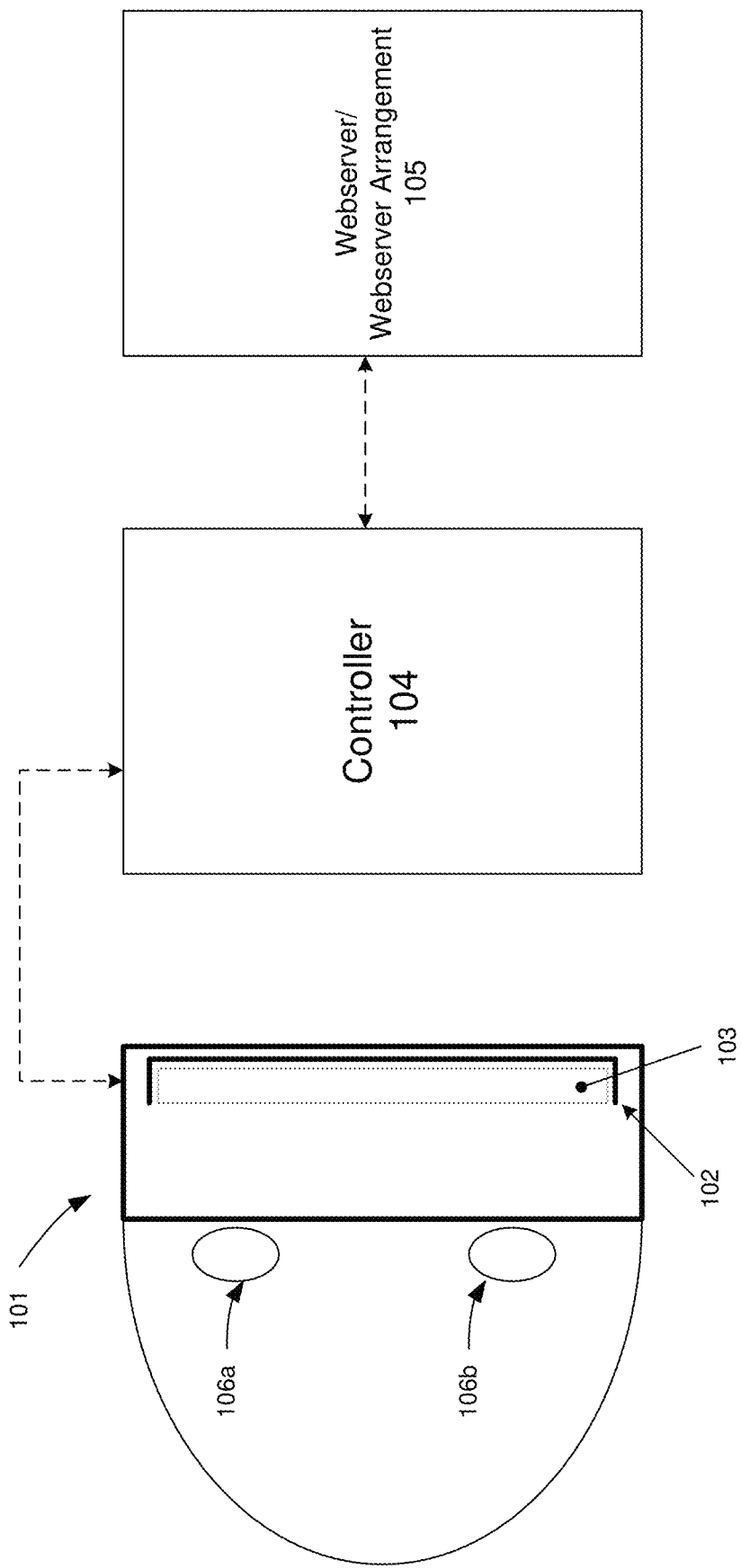
FIG. 1 illustrates the general components used in the present visual assessment VR goggle design.

The exemplification set out herein illustrates particular embodiments, and such exemplification is not intended to be construed as limiting in any manner.

DETAILED DESCRIPTION OF THE INVENTION

The following description and the drawings illustrate specific embodiments sufficiently to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

In general, the present design is broadly directed to a design that employs virtual reality equipment in conjunction with a display device, such as a smartphone, wherein the position of the smartphone relative to the user may be changed to accommodate different ocular or visual tests. In one instance, different images are provided to the user, and he may view them using virtual reality equipment and may recount observations which may be transmitted to a health care provider in any reasonable manner, including by speaking over a phone or VOIP network, use of speech recognition to convert the spoken words to text and making decisions based on the entry, recording responses and transmitting the recorded responses to the health care provider, or otherwise. In this manner, persons with limited mobility or access to health care providers such as optometrists or neurologists can observe, assess, and diagnose patients who would otherwise be unable to be examined.

The present design includes a set of specifically designed or modified Virtual Reality (VR) goggles that can be employed in a specific manner to test the vision and mental status of patients, including certain neurological disorders in both healthcare and non-healthcare settings. The device may include a set of VR goggles used for visual testing or a set of VR goggles adapted to receive a smartphone and using the smartphone to determine distance from a user's face and perform visual testing. When testing vision, the present device can be used as a visual acuity system, visual fields system, visual refractor, and can be employed to assess contrast sensitivity. The system may also be employed to test neurological disorders such as concussions and mental status such as impaired driving skill. The present design facilitates easy measurement of human eye attributes and characteristics for various types of visual conditions, and allows for the observation and analysis of mental status and neurological disorders. The device can be used in healthcare and non-healthcare settings.

Of note in one embodiment of the current design, namely the embodiment employing a computing device such as a smartphone, is the use of a visual separator provided to prevent optical crosstalk when conducting tests on a single eye, as well as a feature or modification that includes a known optical element positionable in front of a camera of a smartphone employed in the design, such as "locked into" the VR goggles, such that the system can determine the precise distance the display screen is from the housing, from which the distance between user eye(s) and smartphone may be determined. Other implementations may be employed, including a set of VR goggles that performs visual testing in accordance with the descriptions herein without the use of a smartphone or other inserted computing device. Further, the present design may include a controller device used to control a visual test using the test device (VR goggles as disclosed herein). In one instance, the controller, which is optional, may be employed by medical personnel who may make decisions and record information regarding the tests administered.

As discussed, two general types of VR goggles may be employed in accordance with the current design. The first type is a set of virtual reality goggles having a holder configured to receive a smart phone type device such that a user can insert the smart phone in the VR goggles in front of the user's eyes. The smart phone in this arrangement performs processing and display functionality. The second type of VR device does not employ a separate computing device such as a smartphone, but is provided with a computing system that operates to provide testing and assessment functionality as described herein using VR goggles. In other words, this second embodiment displays visual indications or test elements using VR goggles, and the other elements of the system assess patient eyesight and/or health. In this document, the term "test device" is employed in situations to represent one or both of the first and second types of VR arrangements.

FIG. 1 illustrates the general components of the current design. From FIG. 1, goggles 101 may be provided with device holder 102 that holds device 103, such as a smartphone. Goggles 101 may be connected in some manner, wired or wirelessly, to controller 104, which controls the goggles 101 and/or device 103. Controller 104 may be connected to webserver 105, representing a computing network that may offer storage and/or processing for use with the other components shown. In one instance, controller 104 may either be optional and goggles 101 and/or device 103 can be directly controlled by webserver 105. Webserver 105 may provide the control described herein, but such functionality may be provided by controller 104. Eyes of a user or patient 106a and 106b are represented. Connections illustrated may or may not be present and may be wired or wireless.

A typical VR headset may include elements such as a securing slot and/or strap to secure the device to the user, foam cushioning between the device, typically made of plastic and the user, with certain controls provided, such as a "back" key for the user to go back, a touchpad for purposes of controlling certain visual representations, and controls such as a volume key to control volume, and a touchpad or other control mechanism. As noted, the VR goggles may include a front cover that accommodates a smartphone and may have lenses directing visual smartphone representations to individual eyes of the user. The headset may include locking mechanisms that lock or otherwise secure the smartphone in a known position within the goggles, and may be connectable to a power source, USB source, or other connections may be provided. An example of a device that may be employed in the current design is the Samsung Gear VR device.

Figure 2:
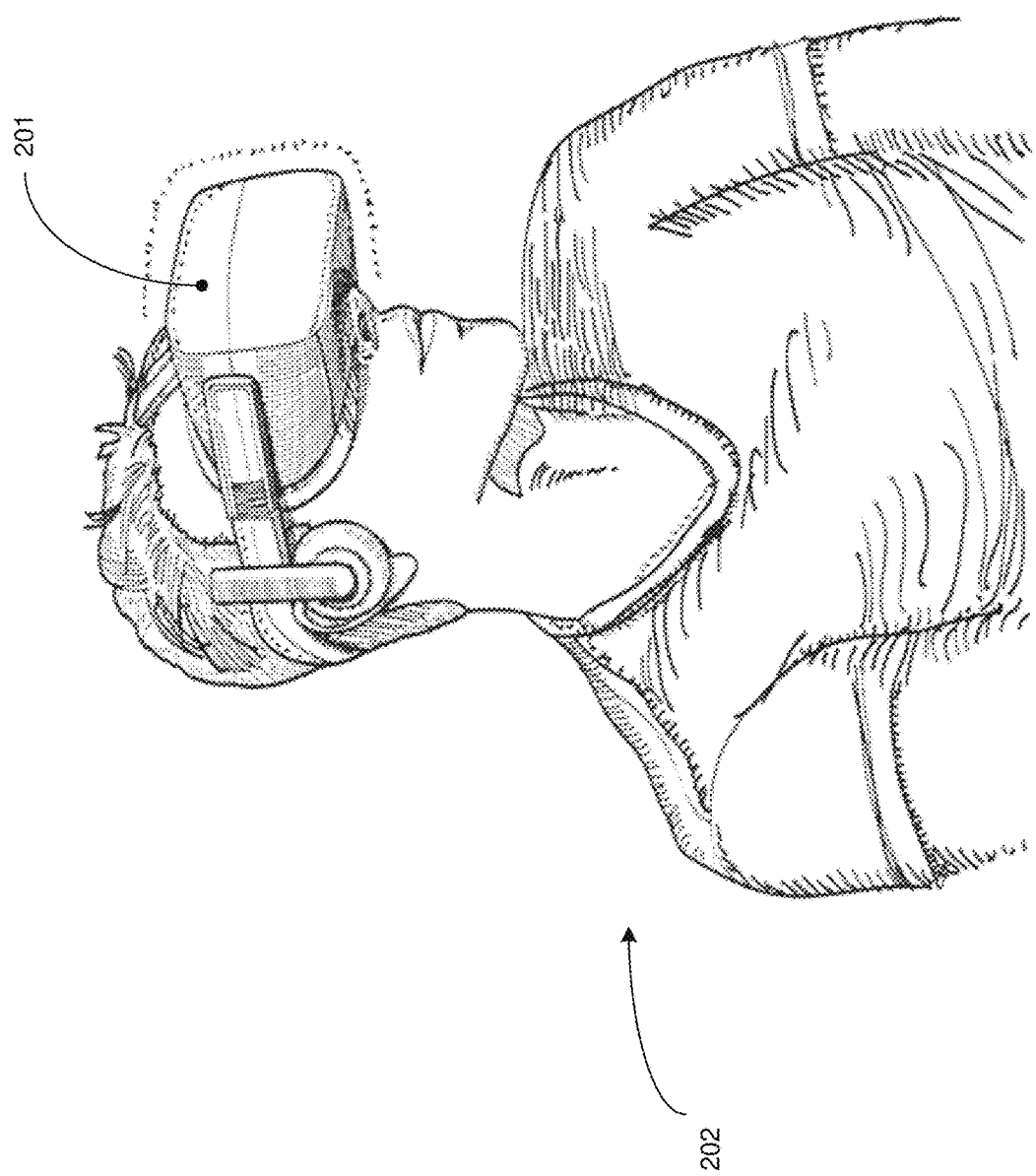
FIG. 2 is a representation of a user or patient wearing VR goggles.
Figure 3:
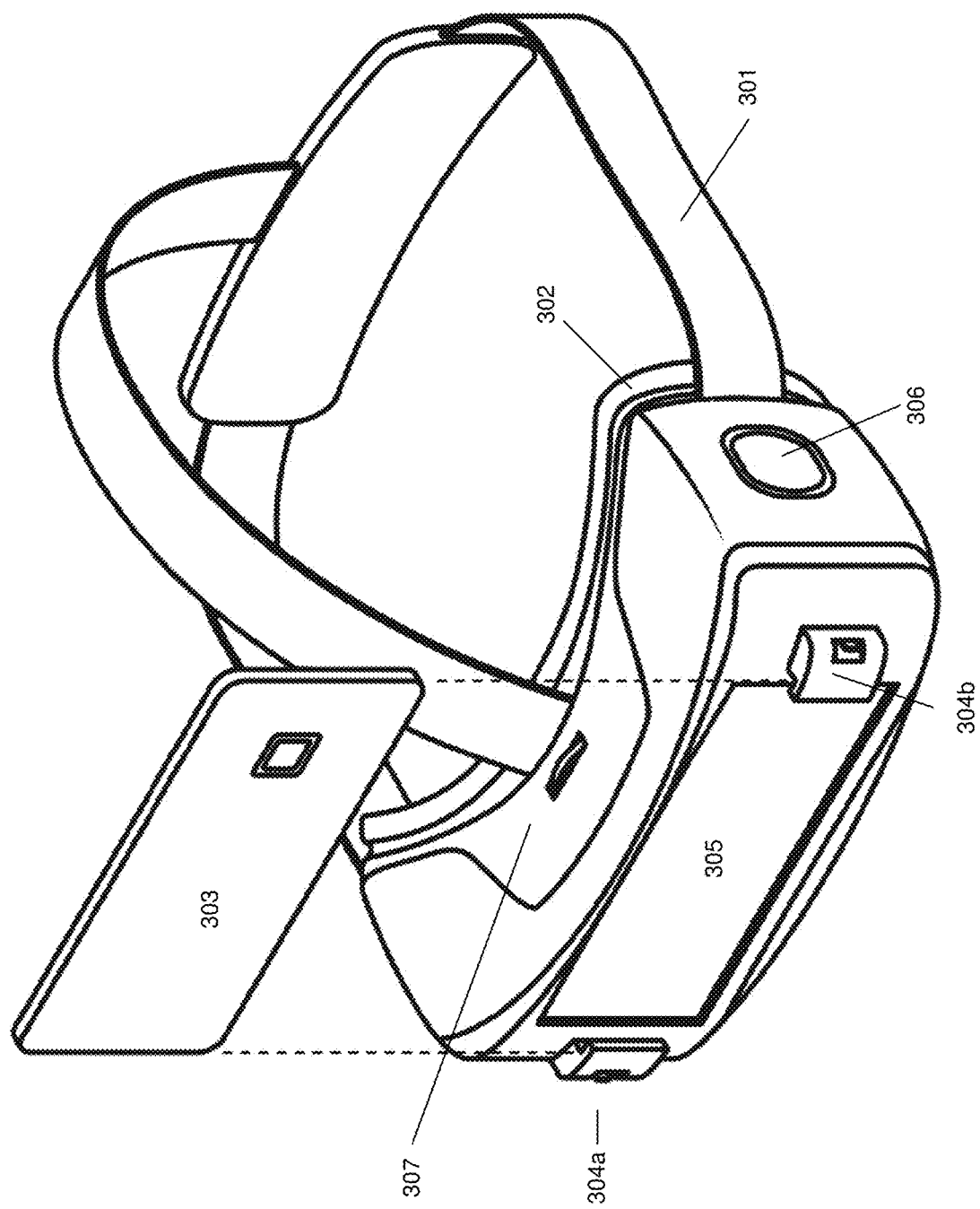
FIG. 3 is a general representation of VR goggles employable according to the present design.

FIG. 2 illustrates a VR headset 201 affixed to a user 202. FIG. 3 is a general representation of a VR headset including a strap 301, wherein a side strap and top strap arrangement is provided in this configuration, as well as foam cushioning 302, a smartphone 303, holding elements 304a and 304b in this view, a forward opening or window 305, a control button 306 which may be a single on/off switch or a multiple way, such as four way selectable switch, and a focus wheel 307 used to alter position of components in the device relative to the user. In one instance or embodiment, such a focus wheel may bring a smartphone closer to or farther from the user by moving the holding mechanism forward and back. Other elements may be provided, such as USB connectivity and a cover secured to the front of the device.

The present design modifies a stock or standard set of VR goggles in two major ways. First, the administering of ocular tests requires isolating the eyes so that testing can be performed on one eye without light crosstalk between eyes or light passing to the other eye. Thus one embodiment of the goggles in accordance with the present design employ a barrier between the eyes not normally found in the art, such as a wall protruding in the direction of the nose.

Figure 6:
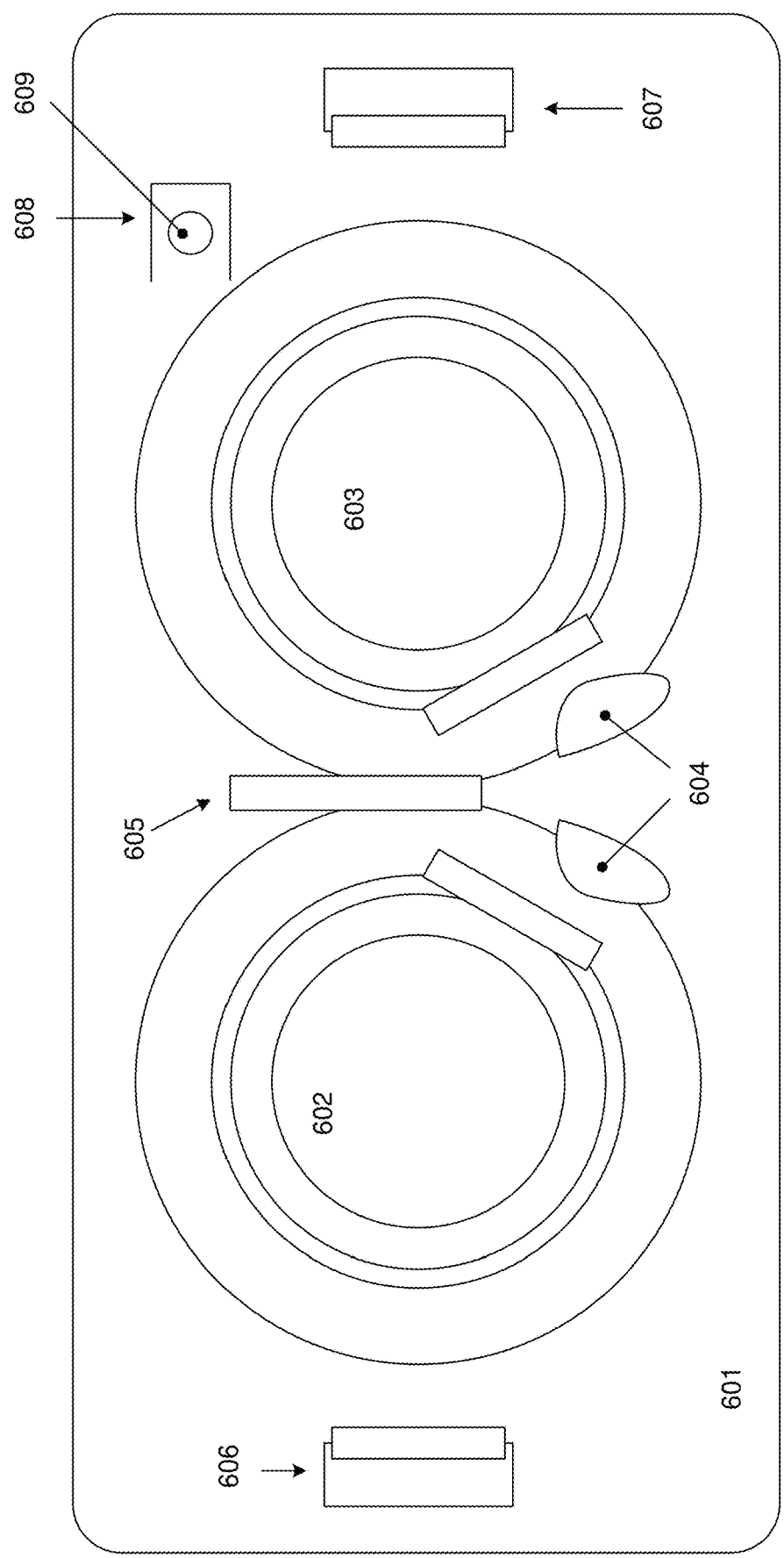
FIG. 6 illustrates a design in accordance with the present teachings.

FIG. 6 illustrates a representation of a set of VR goggles that is not to scale and is generally suggestive in nature, not to scale, and presented for teaching purposes with regards to the current design. From FIG. 6, a plastic housing 601 is provided with eye pieces 602 and 603. Nose pieces 604 are provided to rest on the user's nose. Barrier 605 has been added to the standard set of VR goggles to prevent visual crosstalk, while securing elements 606 and 607 are used in this embodiment to secure a smartphone. Opening 608 represents an opening cut or formed in the plastic of the VR goggles in this embodiment, i.e. in the plastic housing 601, where optical item 609 is provided as a reference and positioned in front of where a camera of a smartphone would be located when provided in the device, specifically in this embodiment using securing elements 606 and 607. Again, the smartphone camera may receive an image of optical item 609, here a white circle expected to be positioned on a dark background (not shown in FIG. 6). The smartphone camera receiving the image of optical item 609 can then, based on the size of the known optical item 609, determine distance between the smartphone and the headset and the system can determine distance to the user's eye(s).

Figure 7:
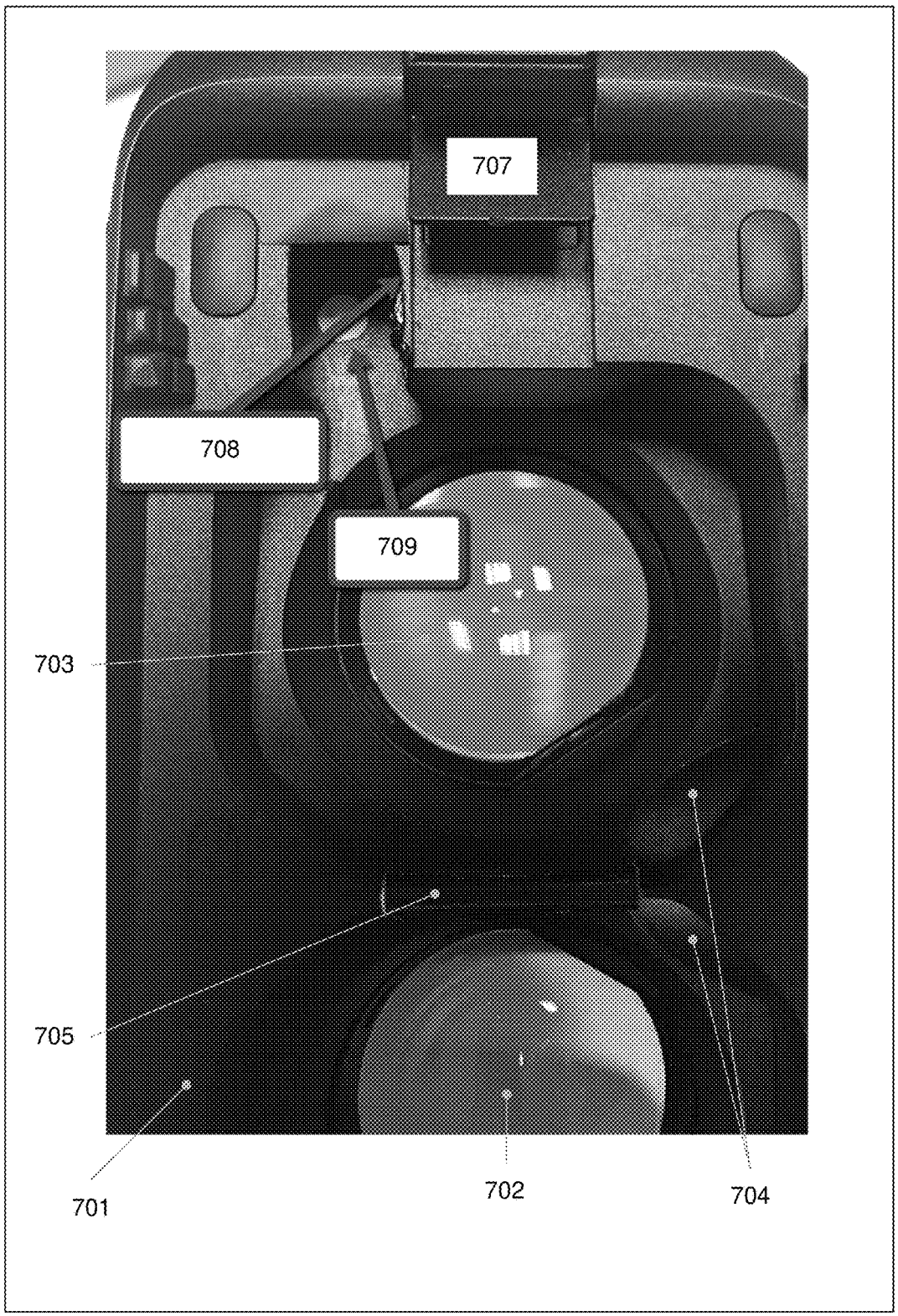
FIG. 7 is a photograph showing an altered version of VR goggles according to one embodiment of the present design.

FIG. 7 is a photograph showing use of the optical item and the modifications made for the current design. From FIG. 7, the plastic housing 701 is provided with eye pieces or lenses 702 and 703. Nose pieces 704 are provided to rest on the user's nose. Barrier 705 is added to the standard set of VR goggles to prevent visual crosstalk, while securing element 707 is shown in this representation and is employed to secure a smartphone (not shown). Opening 708 represents an opening cut or formed in the plastic of the VR goggles in this embodiment, i.e. in the plastic housing 701, where optical item 709 is provided as a reference and positioned in front of where a camera of a smartphone would be located when provided in the device, specifically in this embodiment using securing element 607 and a matching securing element not shown in this representation.

A patient training module may be provided with the test device. Such a patient training module may include an interactive video that may be viewed by the patient/user before the start of testing on the VR goggle device so he can understand how to take the test being administered.

Thus the test device may include virtual reality goggles worn over the eyes of a patient or user for visual testing. The VR goggles may include a smartphone in one embodiment. Another device, such as a separate tablet or smart phone, may be used as a controller and may be provided to medical personnel to manage the test. Separate control functionality may be provided on a computing device connected or connectable to the system, such as a smartphone, tablet, or PC owned by, assigned to, or maintained by medical personnel. The medical staff may provide patient details and select a required test. As the test proceeds, results or other information determined by the test device may be transmitted to the controller. A website specific to the medical entity may be established and provided whereby a detailed database of patients, test reports, and other information can be maintained. The controllability of the test may be provided remotely, such as by a web site or webserver without the use of a controller. Medical personnel can enter test preferences, such as type of test, using the controller and/or website/webserver, and such test preferences may include attributes such as eye to be tested and patient information. The controller, website, and/or webserver can also be used to start, stop, pause and resume the test. The controller unit can allow the use of the device when internet access is not available through peer-to-peer communication (P2P) between the controller and test device. The results of tests captured while internet access is not available may be synchronized with the webserver at a later time, when the controller connects to the internet.

The test device may be continually updated to adjust scene update rates to lower power consumption, extend battery life and prevent overheating. Scene interlacing may be employed to increase effective dynamic range of system. Scene interlacing uses two different frames that are displayed in alternating fashion, thus enhancing the dynamic range of the image formed by our brain.

When used in a non-medical office situation, such as a home setting, the test device again includes VR goggles worn over the eyes for visual testing. A controller is typically not employed, but the VR goggles may or may not include a smartphone or similar device as described herein. The patient may be provided with a login system, such as a website running on a web server or server arrangement, whereby the user/patient can login and start the test and test results can be evaluated by the doctor/staff as the test is ongoing or at a later time.

In some of the tests described below, and as discussed previously, the system needs to establish the distance from the image plane (display) to the user in order to make accurate readings and measurements to successfully assess the health of the patient. The test device may include a focus adjustment wheel that moves the smartphone toward and away from the user's face. The user/patient may use the wheel to move the screen back and forth until the patient can see a clear image. In addition to the eye-surface measurement techniques discussed above, a slot can be provided in the VR goggles and a pre-determined shape of specific color may be provided in the slot. For a test device comprising VR goggles that incorporate a smartphone, the front camera of the smartphone phone would be positioned to photographically capture this slot, or in other words, the camera function of the smartphone would be positioned to photograph the slot. Once the smartphone camera photographs the slot/shape, the size of the shape determines the distance between the smartphone and a known part of the VR goggles. From this, and based on the fact that face shapes are generally similar and a face positioned in the headset is oriented in a known or generally known configuration, the system can determine distance between the smartphone and the user's eye. Certain anomalies may exist, such as a patient/user whose right eye is a slightly different distance than her left eye from the smartphone. Such features can be determined, assessed, and compensated for by medical personnel, or the differences may be considered minimal, or one eye may be tested at a time. Additionally or alternately, the system may offer a calibration functionality used to determine what the user sees in a given scenario to determine the distance to each individual eye.

Some of tests can take time to complete and the patient can become drowsy or sleepy during the test. Tactile lost attention correction can be used, in the form of a vibration applied to the goggles or smartphone, to gently nudge the patients if it is detected that they are not responsive to the tests at any point during the testing period. If the patient loses focus while performing tests, the system may sense the inattention or inactivity and may provide a shaking function in the test device intended to bring the patient back to attention. When testing is completed, the system may allow for the test device to be turned off using the controller. Volume can also be regulated during the test using the controller.

Associated System and Connectivity

With respect to connectivity and connectability of the device, in online mode the VR goggles (referred to herein at times as the "test device," but representing either a VR device with or without smartphone) are connected to a controller through WiFi or Bluetooth wireless connections. The controller is typically connected to the internet and to, for example, a webserver on the cloud such as webserver 105 may be connected using Wi-Fi and/or typical network connections. In this manner, all patient test results may be recorded and saved on the controller 104 and/or the webserver 105. Data can also be transferred using mobile hotspot.

Offline mode is when the controller 104 is not connected with the webserver 105 or otherwise networked. In this arrangement, the flow of communication between the test device or goggles and the controller may be via Bluetooth or hotspot technology or other communication means known in the art, where data may be stored in a local database on the controller. When internet connectivity is available for the controller, a connection may be made with the webserver, the controller may transmit data to the webserver and such data may be stored via a synchronization type process between a local (controller) database and the web based database on the webserver.

Thus for an online or connected arrangement, Wi-Fi networking may be used to communicate data between the test device and controller, and the system transmits data and reports from the controller to the webserver. For a mobile hotspot, when Wi-Fi connectivity is unavailable, data may be transferred between the test device and the controller using a mobile device as a hotspot. This mobile device can be the controller or a separate device. Using the Hotspot interface, data from the test device can be transferred to and from the controller and can be stored on the webserver. For Bluetooth, the test device and controller may be connected using Bluetooth where the test data is stored and synced with the webserver on the cloud using the Wi-Fi connection between the controller and the webserver.

In an offline situation, for Wi-Fi, the test device sends test data and reports to the controller using Wi-Fi connection and it is the data is saved in a local database on the controller. For mobile hotspot, the test device may send data and reports to the controller from the test device, when Wi-Fi is unavailable, using cell phone connectivity offered by the test device as a Hotspot. The controller can also enable a mobile Hotspot to communicate with the test device. In a Bluetooth situation, the test device transfers data, such as test data, to the controller using a Bluetooth connection. The data is stored on the controller and may be transferred to the webserver once an internet connection is available.

The present design may turn the test device on and off remotely using push notifications. The system conserves power, thereby increasing the number of tests administered per battery cycle. When the test device is not in use, the test device may shut off using wireless commands and/or push notifications from the controller, minimizing the need for a person to monitor and interact with the test device. The controller may turn off the test device using a direct command via Bluetooth, Wi-Fi or mobile Hotspot, or even manually. The webserver may send push notifications to turn on and/or turn off the test device using push notifications sent using Wi-Fi or a mobile Hotspot to the test device.

The IP address of the test device may change when moved from one network access point to another. The controller can transmit a push notification to the test device using its MAC address, to query its current IP address, causing the test device to report its local IP address to the webserver, for example, which may relay this information to the controller to establish a wireless connection between the controller and the test device.

The system may control volume on the test device locally, by the user, or remotely using direct commands from the controller to the test device. The system may employ some level of processing or artificial intelligence to assess and predict reference parameters dynamically during a test. Previous patient test results may be collected, analyzed, and used to predict data values, expected responses, areas of difficulty that may be assessed further, and so forth. Such analysis and prediction may reduce the time needed to obtain test results, and in some instances the system may skip redundant tests or assessments of reference data points. As an example, if a person is being tested for color blindness and she exhibits color blindness possibilities in the red-green range but no other range, tests can be focused on red-green color blindness assessments only and can exclude other color blindness tests. This avoids having the person run through scores of tests that certainly or highly likely will not be applicable to him or her.

The system may also detect the distance from the VR display screen to the patient. In one instance this can be accomplished using the mobile camera on the smartphone device. The camera may photograph a target and the number of pixels associated to the target on that image is analyzed. The higher the detected pixel count is in the photograph, the closer the distance between the camera and the target. Other methods of measuring distance may be employed, including use of infrared (IR) lasers or diodes, ultrasound range finder, and/or magnetic range finder. Distance measured is the distance from the VR display screen to the patient, such as placing a known object on the user at a known point (forehead, nose, etc.) and photographing the known object, with an indication of where on the user the known object is placed. From this, the system may determine the distance between the screen and the user's eye. Facial mapping technology may be employed, with the system mapping the user's face (such functionality may be provided on a smartphone or separate device) and again placing a known object on the user's facial region when the smartphone and smartphone camera are in a known position. If the known object size is assessed, the system may compute the distance between the user's eye and the smartphone camera, and may compute relative position(s) using facial mapping and knowledge of the construction of the phone the precise distance between smartphone display and eye. Other forms of distance assessment may be employed.

The importance of knowing the distance between the user's eye and the surface is to have an ability to precisely assess user ocular capabilities. Even fractions of inch differences can, in certain instances, radically influence testing and the results of testing.

Distance may be sent from the test device to the controller and may be displayed to the user. This value can be in units of length (i.e. millimeters) or diopters of vision correction, and values such as raw pixel count may also be assessed and reported. Distance information is used to set proper display position based on patient's refraction, i.e. his or her current prescription power. Such a distance measurement eliminates the need for the test subject to use corrective lenses or glasses during the test. For some patients, the distance may be predetermined and set according to their current prescription glasses before the test is taken. Such a distance setting can be established using the controller without the user having to wear the VR headset or can even be done while the headset/test device is worn using the focus adjusting wheel. The distance may be set or changed using the controller, or directly by the controller, depending on the test being conducted. Some tests require corrected vision and hence corrected distance while some require uncorrected vision or uncorrected distance.

Testing

The VR goggle test device can be used to check the patient's visual capability. Visual capability is commonly measured as two numbers, such as 20/20, 20/10, 20/40, etc., where the first number refers to the distance in meters the chart is from the patient and the second number is the distance in meters at which a person with no impairment should be able to see the chart.

The user or medical caregiver selects the eye to be tested and the eye chart is placed only in front of that eye in the VR goggle test device, i.e. viewable at the requisite distance via the VR goggles. This ensures that the patient is not using the other eye to recognize the images/characters. At least two types of visual acuity eye tests can be administered, namely the automated visual acuity test and monitored visual acuity test.

Figure 4:
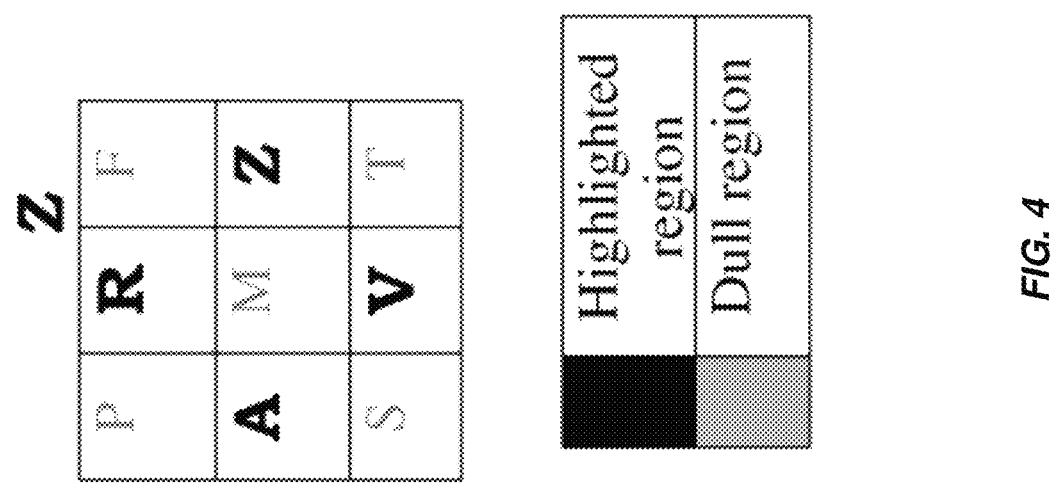

The Automated Visual Acuity Test employs a test as shown in FIG. 4. The test administered is similar to visual acuity testing using a Snellen chart. In the visual acuity check, the patient looks at (gaze input) one of the highlighted regions of the squares that matches the reference image/character above (in this case, the dark letter "Z") to select the correct letter. Selection takes place using what is called "gaze input." As the test progresses, the letters become smaller and smaller and the patient stops when he/she is unable to recognize the image/character. The system then determines vision status based on the letters correctly and incorrectly selected.

In a monitored visual acuity test, the user or health care professional may select a particular line such as a sequence of characters of different size, wherein selection may be made via the controller, and the system, via the smartphone, highlights the same line in the patient's VR goggle for him/her to read. Such a line of text is shown in FIG. 5.

In an unmonitored visual acuity test, the system may employ voice recognition for patient feedback. In the case of the visual acuity test, the patient may be in a room and may begin the test, and the system may record his/her responses and may progress through the test based on voice feedback. Thus the system will typically include a microphone, such as in the smartphone or separately and connected to the system. In the visual acuity test situation, the system highlights a symbol/icon/letter. The patient may say the name of the symbol/icon/alphabet aloud. The system receives this audible response and may convert the response to text using voice recognition and the result is compared to the reference input to check for correctness.

The system can employ visual selection for patient feedback. Again, the system highlights a symbol/icon/letter. The patient attempts to match the highlighted symbol/icon/letter to one of the options provide on the screen. Gaze input is used to make this selection. Gaze input is the use of the patient's view on the options to identify the correct option and is provided on various VR goggles. In essence, the goggles include a visual evaluation method and device, such as a camera, that assesses the position of the user's eye or eyes (iris position, for example) and based on the angle of the eye or eyes determines what he/she is gazing at. Alternately, head position may be sensed via a device such as a gyroscope; if the user is looking right, the system determines he/she is looking right. Such gaze input or gaze assessment determines whether the patient is able to recognize the desired image amongst the options given by pointing to the image.

The present system may be used as a visual fields test system to test sensitivity to stimuli in different areas of vision. The test starts with central fixation of light in a direction where the patient is expected to look for the test to proceed. The system then provides light of different intensities and angles to the patient. The system may employ lights of different colors so that patient's sensitivity to different frequencies can be assessed. The patient can confirm the visibility of light by pressing an external selection button, such as a button provided on the goggles, or by looking (gaze input) in the direction of light. The system places lights in front of the eye being tested and runs the test on that eye exclusively.

The system assesses and makes corrections based on a test of distance between the VR display screen and the patient's eyes, potentially using the controller. In visual field tests the patient looks at a provided fixation point. The fixation point is a reference point that is provided for the patient to look at during the test. Fixed position gaze tracking may be employed, where the point of focus is fixed. If the patient moves his head to look away from the point, the test is stopped. Alternately, the system may employ moving position gaze tracking by slowly moving a fixation dot within the VR display and asking the patient to continually keep focus on the fixation dot. Two reference dots of different color (red and green) are typically employed. Red is the reference dot onto which the green dot should coincide in order to begin the test to ensure proper focus during the test.

The system may also expand the field of view by positioning the fixation point at different locations in the scene and performing the test. The system may also or alternately employ gaze tracking to check how far an eye can move to reach maximum field of view.

Internal IR based gaze tracking cameras may be employed to monitor patient's pupil location and ensure the patient is focusing on the fixation point in order to produce the best measurement results from the tests.

Other ocular and optical assessment tests may be provided using the current design. Such additional tests may include a contrast sensitivity test, which measures ability to distinguish between light versus dark (contrast) finer increments. It is beneficial in situations where the patient is exposed to and has difficulty with low light, fog, or glare. Even if a patient has 20/20 visual acuity, he can have an eye or health condition that may diminish contrast sensitivity.

The test employed includes measurement of both size (spatial frequency) and contrast to plot a person's contrast sensitivity function (CSF). Sine-wave grating targets with thicker bars represent low spatial frequencies; targets with thinner bars represent higher spatial frequencies. Contrast sensitivity function essentially is plotting of a curve that defines the lowest contrast level that the patient can detect for each spatial frequency tested.

Generally, objects with high spatial frequencies (sinewave gratings with very thin bars) must have significantly higher contrast than objects with lower spatial frequencies (gratings with medium-width bars) to be detected by the human visual system.

The system may also be used to test mental status and neurological disorders associated with vision. Most commonly, some eye tests are used to detect concussions. Checks using the present system may include checking the cranial nerves of the patient, where the system moves a visual representation of an object, such as a pen, in all directions and asks the patient to follow the pen with his/her eyes, evaluating peripheral vision, and checking the pupils by focusing light for a short period of time to check for unwanted constrictions.

The system may predict consequent sets of values based on the test values obtained from previous patients. For example, if 60 of 64 patients have difficulty reading a sixth line of characters after being unable to read the fifth line of characters, the system may omit the test requirement for the patient to read the sixth line. Alternately, if the patient exhibits color blindness in the red spectrum but in no other spectrum, previous patient responses with red spectrum issues can be assessed and if appropriate, color blindness tests can be focused on red spectrum issues and other tests may be omitted. Such functionality can reduce the time needed for testing.

Thus the present design may include an apparatus comprising virtual reality goggles affixable to a patient, the virtual reality goggles comprising two central lenses employed to be positioned over the patient's eyes, securing means configured to secure a computing device to the set of virtual reality goggles, and means for determining a distance between the patient's eyes and the computing device. The set of virtual reality goggles is employable to test visual attributes of the patient.

According to another aspect of the present design, there is provided an apparatus comprising virtual reality goggles affixable to a patient, the virtual reality goggles comprising two central lenses employed to be positioned over the patient's eyes and means for determining distance between the patient's eyes and the two central lenses. The virtual reality goggles are employable to test visual characteristics of the patient.

According to a further aspect of the present design, there is provided a system for testing ocular characteristics of a patient, comprising a controller configured to coordinate and perform visual testing, virtual reality goggles connectable to the controller and affixable to the patient, the virtual reality goggles comprising two central lenses employed to be positioned over the patient's eyes, and means for assessing position of the virtual reality goggles relative to the patient's eyes, including distance from the patient's eyes to a display element provided with the virtual reality goggles. The controller provides signals to and receives signals from the virtual reality goggles to test and assess visual attributes of the patient.

The devices, processes and features described herein are not exclusive of other devices, processes and features, and variations and additions may be implemented in accordance with the particular objectives to be achieved. For example, devices and processes as described herein may be integrated or interoperable with other devices and processes not described herein to provide further combinations of features, to operate concurrently within the same devices, or to serve other purposes. Thus it should be understood that the embodiments illustrated in the figures and described above are offered by way of example only. The invention is not limited to a particular embodiment, but extends to various modifications, combinations, and permutations that fall within the scope of the claims and their equivalents.

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A system for testing ocular characteristics of a patient; comprising:

a controller configured to coordinate and perform visual testing;

virtual reality goggles connectable to the controller and configured to be affixed to the patient, the virtual reality goggles comprising two central lenses employed to be positioned over the patient's eyes, the virtual reality goggles comprising an optical separator element positioned between the two central lenses, wherein the virtual reality goggles are configured to receive a computing device comprising a display and a camera; and a webserver arrangement configured to receive patient test results from the controller;

wherein the controller tests and assesses visual healthcare attributes of the patient and provides healthcare test signals to the virtual reality goggles comprising at least one of visual acuity healthcare test signals, visual fields healthcare test signals, visual refractor healthcare test signals, and contrast sensitivity healthcare test signals, wherein the controller is further configured to provide a visual healthcare attribute test image to a first central lens of the two central lenses while simultaneously refraining from providing any visual healthcare attribute test images to a second central lens of the two central lenses;

wherein when the virtual reality goggles maintain the computing device, the computing device provides healthcare test signals to the display and toward the patient and the camera assesses patient eye position when the patient views the healthcare test signals;

and further wherein the controller is configured to transmit patient visual attributes test results to the webserver arrangement.

2. The system of claim 1, wherein at least one of the computing device and the virtual reality goggles are configured to determine, based on size of a visual reference item assessed using the camera of the computing device, distance between the display of the computing device and at least one eye of the patient.

3. The system of claim 1, wherein the system is configured to selectively alter an internet protocol (IP) address of the virtual reality goggles moving from communication with one network access point to communication with another access point, and is further configured to use push notifications to retrieve a new IP address of the virtual reality goggles.

4. The system of claim 1, wherein the virtual reality goggles are configured to provide a tactile function applicable to attempt to reinstate attention of the patient.

5. The system of claim 1, further comprising an audio sensor wherein the system is configured to receive audio commands via the audio sensor and act based on the audio commands received.

6. The system of claim 1, further comprising means for assessing position of the virtual reality goggles relative to the patient's eyes, including distance from the patient's eyes to the display when the computing device is provided with the virtual reality goggles.

7. The system of claim 1, wherein the optical separator element comprises a vertical wall positioned and configured to eliminate visual crosstalk.

8. A system for testing ocular characteristics of a patient, comprising:
  a controller configured to coordinate and perform visual testing of the patient;
  virtual reality goggles connectable to the controller and configured to be affixed to the patient, the virtual reality goggles comprising two lenses and an optical separator element positioned between the two lenses, wherein the virtual reality goggles are configured to receive a computing device comprising a display and a camera; and
  a webserver arrangement configured to receive patient test results from the controller;
  wherein the controller is configured to test and assess visual attributes of the patient and is configured to provide healthcare test signals to the virtual reality goggles comprising at least one of visual acuity healthcare test signals, visual fields healthcare test signals, visual refractor healthcare test signals, and contrast sensitivity healthcare test signals, wherein the controller is further configured to provide a visual healthcare attribute test image to a first lens of the two lenses while concurrently refraining from providing any visual healthcare attribute test images to a second lens of the two lenses;
  wherein when the virtual reality goggles maintain the computing device, the computing device provides healthcare test signals to the display and toward the patient and the camera assesses patient eye position when the patient views the healthcare test signals;
  and further wherein the controller is configured to transmit patient visual attributes test results to the webserver arrangement.

9. The system of claim 8, wherein the two lenses are positionable over the patient's eyes.

10. The system of claim 8, wherein at least one of the computing device and the virtual reality goggles are configured to determine, based on size of a visual reference item assessed using the camera of the computing device, distance between the display of the computing device and at least one eye of the patient.

11. The system of claim 8, wherein the system is configured to selectively alter an internet protocol (IP) address of the virtual reality goggles moving from communication with one network access point to communication with another access point, and is further configured to use push notifications to retrieve a new IP address of the virtual reality goggles.

12. The system of claim 8, wherein the virtual reality goggles are configured to provide a tactile function applicable to attempt to reinstate attention of the patient.

13. The system of claim 8, further comprising an audio sensor, wherein the system is configured to receive audio commands via the audio sensor and act based on the audio commands received.

14. The system of claim 8, further comprising means for assessing position of the virtual reality goggles relative to the patient's eyes, including distance from the patient's eyes to the display when the computing device is provided with the virtual reality goggles.

15. The system of claim 8, wherein the optical separator element comprises a vertical wall positioned and configured to eliminate visual crosstalk.

16. A system for testing ocular characteristics of a patient, comprising:
  a controller;
  virtual reality eyewear connectable to the controller and configured to be affixed to the patient, the virtual reality eyewear comprising two lenses and an optical separator element positioned between the two lenses, wherein the virtual reality eyewear is configured to receive a computing device comprising a display and a camera; and
  a webserver arrangement configured to receive patient test results from the controller;
  wherein the controller is configured to test and assess visual attributes of the patient and is configured to provide healthcare test signals to the virtual reality eyewear comprising at least one of visual acuity healthcare test signals, visual fields healthcare test signals, visual refractor healthcare test signals, and contrast sensitivity healthcare test signals, wherein the controller is further configured to provide a visual healthcare attribute test image to a first lens of the two lenses while concurrently refraining from providing any visual healthcare attribute test images to a second lens of the two lenses;
  wherein when the virtual reality eyewear holds the computing device, the computing device provides healthcare test signals to the display and toward the patient and the camera assesses patient eye position when the patient views the healthcare test signals;
  and further wherein the controller is configured to transmit patient visual attributes test results to the webserver arrangement.

17. The system of claim 16, wherein the two lenses are positionable over the patient's eyes.

18. The system of claim 16, wherein at least one of the computing device and the virtual reality eyewear are configured to determine, based on size of a visual reference item assessed using the camera of the computing device, distance between the display of the computing device and at least one eye of the patient.

19. The system of claim 16, wherein the system is configured to selectively alter an internet protocol (IP) address of the virtual reality eyewear moving from communication with one network access point to communication with another access point, and is further configured to use push notifications to retrieve a new IP address of the virtual reality eyewear.

20. The system of claim 16, wherein the virtual reality eyewear are configured to provide a tactile function applicable to attempt to reinstate attention of the patient.

21. The system of claim 16, further comprising an audio sensor, wherein the system is configured to receive audio commands via the audio sensor and act based on the audio commands received.

22. The system of claim 16, further comprising means for assessing position of the virtual reality eyewear relative to the patient's eyes, including distance from the patient's eyes to the display when the computing device is provided with the virtual reality eyewear.

23. The system of claim 16, wherein the optical separator element comprises a vertical wall positioned and configured to eliminate visual crosstalk.

\* \* \* \* \*